United States Patent [19]

Mantelle

[11] Patent Number: 5,234,957
[45] Date of Patent: Aug. 10, 1993

[54] COMPOSITIONS AND METHODS FOR TOPICAL ADMINISTRATION OF PHARMACEUTICALLY ACTIVE AGENTS

[75] Inventor: Juan A. Mantelle, Miami, Fla.

[73] Assignee: Noven Pharmaceuticals, Inc., Miami, Fla.

[21] Appl. No.: 813,196

[22] Filed: Dec. 23, 1991

Related U.S. Application Data

[63] Continuation-in-part of Ser. No. 661,827, Feb. 27, 1991, abandoned.

[51] Int. Cl.$^5$ ............................................. A61K 47/32
[52] U.S. Cl. ......................... 514/772.6; 424/485; 424/486; 424/487; 424/488; 514/781; 514/782
[58] Field of Search ............... 424/435, 443, 447, 449, 424/450, 484, 485, 486, 487, 488; 514/818, 947, 781, 782

[56] References Cited

U.S. PATENT DOCUMENTS

| | | | |
|---|---|---|---|
| 2,142,537 | 1/1939 | Tisza | 167/52 |
| 2,277,038 | 3/1942 | Curtis | 167/52 |
| 2,352,691 | 7/1944 | Curtis | 260/472 |
| 2,501,544 | 3/1950 | Shrontz | 128/268 |
| 3,249,109 | 5/1966 | Maeth | 128/268 |
| 3,632,740 | 1/1972 | Robinson | 424/28 |
| 3,640,741 | 2/1972 | Etes | 106/170 |
| 3,814,095 | 6/1974 | Lubens | 128/260 |
| 3,972,995 | 8/1976 | Tsuk | 424/28 |
| 4,302,465 | 11/1981 | Ekenstam | 424/267 |
| 4,307,075 | 12/1981 | Martin | 424/28 |
| 4,466,973 | 8/1984 | Rennie | 424/267 |
| 4,529,601 | 7/1985 | Broberg | 514/626 |
| 4,572,832 | 2/1986 | Kigasawa | 424/19 |
| 4,608,249 | 8/1986 | Otsuka | 424/28 |
| 4,615,697 | 10/1986 | Robinson | 604/890 |
| 4,652,060 | 12/1985 | Broberg | 424/28 |
| 4,659,714 | 4/1987 | Watt-Smith | 514/260 |
| 4,675,009 | 6/1987 | Hymes | 604/304 |
| 4,695,465 | 9/1987 | Kigasawa | 424/449 |
| 4,748,022 | 5/1988 | Busciglio | 424/195 |
| 4,765,983 | 8/1988 | Takayanagi | 424/434 |
| 4,789,667 | 12/1988 | Makino | 514/161 |
| 4,867,970 | 9/1989 | Newsham et al. | 424/435 |
| 4,888,354 | 12/1989 | Chang | 514/424 |
| 4,894,232 | 1/1990 | Reul | 424/439 |
| 4,900,552 | 2/1990 | Sanvordeker | 424/422 |
| 4,900,554 | 2/1990 | Yanagibashi | 424/448 |
| 4,937,078 | 6/1990 | Mezei | 424/450 |
| 4,940,587 | 7/1990 | Jenkins | 424/480 |
| 4,981,875 | 1/1991 | Leusner | 514/774 |
| 5,023,082 | 6/1991 | Friedman | 424/426 |

FOREIGN PATENT DOCUMENTS

| | | |
|---|---|---|
| 0002425 | 6/1979 | European Pat. Off. . |
| 0139127 | 5/1985 | European Pat. Off. . |
| 0159168 | 10/1985 | European Pat. Off. . |
| 250187 | 6/1987 | European Pat. Off. . |
| 0331392 | 2/1989 | European Pat. Off. . |
| 363224 | 10/1989 | European Pat. Off. . |
| 217989A1 | 3/1983 | Fed. Rep. of Germany . |
| 52460 | 11/1966 | Luxembourg . |
| WO89/10740 | 11/1989 | PCT Int'l Appl. . |
| 352239 | 12/1972 | Sweden . |
| 1360820 | 7/1974 | United Kingdom . |

OTHER PUBLICATIONS

"Molecular Mechanisms of Local Anesthesia: A Review", by John F. Butterworth, Garry R. Strichartz. Anesthesiology 72:711-754, 1990. Pertinent pp. 720-721.

*Primary Examiner*—Thurman K. Page
*Assistant Examiner*—Carlos Azpuru
*Attorney, Agent, or Firm*—Foley & Lardner

[57] ABSTRACT

A composition for topical application comprising a therapeutically effective amount of a pharmaceutical agent(s), a flexible, finite, pharmaceutically acceptable, bioadhesive carrier, and a solvent for the pharmaceutical agent(s) in the carrier and a method of administering the pharmaceutical agent to a mammal are disclosed.

23 Claims, No Drawings

COMPOSITIONS AND METHODS FOR TOPICAL ADMINISTRATION OF PHARMACEUTICALLY ACTIVE AGENTS

CROSS-REFERENCE TO RELATED APPLICATION

This application is a continuation-in-part of U.S. patent application Ser. No. 07/661,827 filed Feb. 7, 1991, now abandoned, which application is hereby incorporated by reference.

BACKGROUND OF THE INVENTION

1. Field of the Invention

The present invention relates to compositions and methods for the topical administration of pharmaceutically active agents to a mammal in need thereof. More particularly, the present invention relates to anesthesia and local anesthetic agents for topical administration. Still more particularly, the invention relates to a method for the topical administration of an anesthetic agent or a combination of anesthetic agents to prevent or ameliorate pain.

There is no limitation on the type of pharmaceutical agent that can be used in the present invention, provided that it can be absorbed percutaneously. Thus, the pharmaceutical agent includes both drugs that are topically applied for local effects and those which can be administered topically for systemic effects.

2. Description of Background Art

Anesthetic agents are pharmacologically active agents that block nerve conduction when applied in therapeutically effective amounts. They can be used for local or systemic application. Anesthetic agents have been used extensively in the medical field to obtain topical anesthesia. Topical administration or application means the direct contact of the anesthetic with tissue, such as skin or membrane, particularly the oral or buccal mucosa. Previous methods of applying topical anesthetic agents to the skin or mucosa have used "nonfinite" or semi-liquid carriers such as gels or ointments, or "finite" carriers, non-spreading substances which retain their form, e.g. patches, dressings and bandages.

Local anesthetics generally are esters or amides of benzoic acid derivatives, administered either as the free base or the acid-addition salt. Free bases tend to be irritating at high concentrations. Acid-addition salts have low skin permeability.

To be effective, a topical, local anesthetic should contain sufficient concentration of the active agent to produce an anesthetic effect, it should penetrate intact skin or mucosa sufficiently to deliver a therapeutic dose, and it should exhibit rapid onset of anesthetic action and have a prolonged anesthetic effect. In achieving the foregoing, it is often desirable to have the anesthetic agent present in a high concentration to effect a rapid onset and, additionally or alternatively, in excess of the amount that can be immediately absorbed through the dermis at the site of application, so as to prolong anesthesia. On the other hand, the presence of the anesthetic agent in crystalline form may irritate sensitive tissues such as mucosal tissues. This is particularly true with regard to lidocaine.

A number of references disclose local anesthetic compositions. For instance, Swedish Patent Publication No. 352,239 published Dec. 27, 1972 in the name of S. G. Davis et al., assigned to Astra Pharmaceutical Products, Inc., and based on Swedish patent application No 17744/70 filed Dec. 30, 1970, discloses a local anesthetic film containing up to 50% lidocaine in crystallized, microdispersed form. In its final form, this composition lacks a solvent for the anesthetic agent. The preparation is prepared by adding a solution of lidocaine in an organic solvent or an acid addition salt in water, under heat and agitation, to a solution or suspension of a film-forming material, namely carboxymethyl cellulose, polyvinyl alcohol, or a mixture of polyvinyl alcohol and polyvinyl pyrrolidone in water, followed by heating to remove any solvent present.

U.S. Pat. No. 4,937,078 to Mezei, et al. describes a liposome encapsulated local anesthetic or analgesic agent that is said to provide, when applied to the skin or mucous membrane, greater local anesthesia and analgesia than the same agents incorporated in conventional vehicles such as ointments, creams, or lotions. These liposomal films are preferably applied under occlusion.

U.S. Pat. Nos. 4,572,832 and 4,695,465 to Kigasawa and 3,249,109 to Maeth all describe the use of water soluble protein based systems which incorporate anesthetics, and which also contain a tackifier and a polyhydric alcohol solvent. In the compositions of these references, the water soluble protein gives the base its consistency and bulk and serves as an essential vehicle for the incorporation of medicaments and therapeutic agents.

U.S. Pat. No. 4,894,232 to Reül, et al. discloses a base for mucosal or denture adhesive pastes and a process for the preparation thereof. Lidocaine is one possible therapeutic agent suitable for this paste.

U.S. Pat. No. 3,814,095 to Lubens describes an absorbent pad for topical application of an anesthetic agent and having a peripheral adhesive.

It is also known to combine two local anesthetic free bases with different melting points. By mixing the two anesthetic bases, an eutectic mixture has been reported that is liquid at room temperature, making it possible to attain higher concentrations of the active bases.

U.S. Pat. No. 4,888,354 by Chang relates to a combination of the free base and an acid addition salt or a variety of drugs, typically in a liquid carrier, to increase skin penetration rates. Anesthetics, along with a list of other suitable drugs are mentioned. This reference specifically teaches that base and acid-addition forms of the same drug be used in carrier.

U.S. Pat. No. 2,352,691 to Curtis teaches the use of salicylate salts of alkamine esters of amino benzoic acid to enhance the water solubility of anesthetic agents. In one example, this reference discloses a solution of procaine acetyl salicylate containing insoluble anesthetics such as benzocaine, butesin, orthoform, or their salts, in certain glycols which are combined with a volatile solvent, and then used to saturate gauze bandages or other suitable fabrics.

U.S. Pat. No. 2,142,537 to Tisza describes an ointment containing isoamylhydrocupreine in combination with a quick acting local anesthetic to overcome the undesirable irritation caused by the prolonged acting anesthetic isoamylhydrocupreine or its salts. The preparation of Tisza combines short and long acting anesthetic agents. However, such preparation is not provided in a convenient form for topical administration, nor does it appear to contain a high concentration of finely-dispersed drug.

U.S. Pat. No. 4,900,552 by Sanvordeker et al. disclose a trilaminate film suitable for prolonged and sustained delivery of an active ingredient in a buccal cavity. Specifically a hydratable mucoadhesive base layer, a non-adhesive reservoir layer and a water-impermeable carrier film sandwiched between and bonded to the base layer and the reservoir layer form the trilaminate film. This reference generally describes and claims the addition of an active ingredient to the non-adhesive reservoir layer.

U.S. Pat. No. 2,277,038 to Curtis relates to preparations containing a mixture of two or more anesthetic agent salts having different pH values in solution, whereby the pH value of the combined mixture in solution may be adjusted to obtain a higher degree of stability of the solution, and at relatively higher pH, a more rapid onset of anesthetic action. The anesthetic agents in Curtis are not in highly dispersed form and are used in a liquid-soaked fabric.

Procaine salts of different drugs, namely procaine penicillin G, given by intramuscular injection are also known to prolong the antimicrobial action of the antibiotic.

Commonly, prolongation of anesthesia with topical anesthetics has been achieved by the addition of vasoconstrictors, such as the catecolamine, epinephrine, which caused constriction of blood vessels. Since catecolamines are not particularly effective when applied topically, such a prolongation is of minimal usefulness for topical anesthetics. The primary drawbacks of this approach are the potential adverse side effects of catecolamines, and the prolongation itself.

Although many local anesthetic compositions have been proposed, it has been discovered that the incorporation of one or more anesthetic agents in a solvent for the anesthetic agent into a flexible, finite, pharmaceutically acceptable carrier, permits an exceptionally high loading of anesthetic agent in the carrier, permitting more rapid delivery of the anesthetic agent to the dermal membrane Without crystallization of the anesthetic agent which can limit absorption by the skin and which can cause irritation of the skin or other dermal membrane.

It has surprisingly been found that concentrations of substantially dissolved anesthetic agent as high as 50% by weight can be achieved in a system in which the adhesion of the adhesive is not hindered. Prolongation of anesthesia can thus be achieved by increasing the amount of time the composition is applied, without detrimental irritation. The compositions of the present invention are in convenient form for topical application of the anesthetic agents, thereby enabling such anesthetics to penetrate the dermis, for example, intact skin or a mucous membrane. Moreover, the anesthetic action is highly localized. Because the drug is substantially microdispersed in the carrier, it is more readily available for permeation into the skin or dermal membrane.

It still further has surprisingly been found that the use of two different local anesthetic agents, the first in base form and the second in salt form, in a finite, flexible, adhesive, pharmaceutically acceptable carrier, including a solvent for the anesthetic agents, permits the attainment of anesthetic agent concentrations in the final product of up to 50% by weight in microdispersed form, without crystallization of the anesthetic agents which can cause irritation of the skin or other dermal membrane. Thus, in one embodiment, the present invention is in convenient form for topical application of the anesthetic agents, thereby enabling such anesthetics to penetrate intact skin or mucous membranes and have a highly localized effect. Furthermore, the combination of the salt and base forms, advantageously results in rapid onset of anesthetic action with prolonged anesthetic effect.

SUMMARY OF THE INVENTION The invention relates to a composition for topical application comprising:

(a) a therapeutically effective amount of at least one local anesthetic;
(b) a pharmaceutically acceptable solvent for the anesthetic, in an amount from about 5 to about 70 weight percent based on the weight of the whole composition;
(c) in admixture with the anesthetic agent in the solvent, a flexible, finite, pharmaceutically acceptable polysaccharide bioadhesive carrier in an amount from about 20 to about 50 weight percent based on the weight of the whole composition;

wherein the composition is substantially free of water and is substantially water insoluble.

In another embodiment, the composition of the invention is comprised of two anesthetic agents, that is:

(a) a therapeutically effective amount of a first local anesthetic agent in base form;
(b) a therapeutically effective amount of a different, second local anesthetic agent in acid-addition salt form;
(c) a solvent for the first and second local anesthetic agents in an amount from about 5 to about 70 weight percent based on the weight of the whole composition; and
(d) in an admixture with the anesthetic agents in the solvent, a flexible, finite, pharmaceutically acceptable, bioadhesive carrier in an amount from about 20 to about 50 weight percent based on the weight of the whole composition;

wherein the composition is substantially free of water and is substantially water insoluble.

The compositions of the invention may be further include a backing material which conforms to the size and shape of a single dosage of the composition.

The present invention further relates to a method of administering one or more local anesthetic agents to a subject comprising the steps of:

(a) providing a composition comprising a therapeutically effective amount of at least one local anesthetic; a pharmaceutically acceptable solvent for the anesthetic, in an amount from about 5 to about 70 weight percent based on the weight of the whole composition; and in admixture with the anesthetic agent in the solvent, a flexible, finite, pharmaceutically acceptable polysaccharide bioadhesive carrier in an amount from about 20 to about 50 weight percent based on the weight of the whole composition; wherein said composition is substantially free of water and is substantially water insoluble; and
(b) contacting an area of skin or mucous membrane with the composition to administer the local anesthetic.

The invention further relates to a method of administering two local anesthetic agents to a subject comprising the steps of:

(a) providing a composition comprising a therapeutically effective amount of a first local anesthetic agent in base form; a therapeutically effective amount of a different, second local anesthetic agent in acid-addition salt form; a pharmaceutically acceptable solvent for the anesthetic in an amount which ranges from about 5 to about 70 weight percent based on the weight of the whole composition; and in admixture with the anesthetic agent in the solvent, a flexible, finite, pharmaceutically acceptable bioadhesive carrier in an amount which ranges from about 20 to about 50 weight percent based on the weight of the whole composition; wherein said composition is substantially free of water and is substantially water insoluble; and (b) contacting an area of skin or mucous membrane with the composition thereby administering the local anesthetics.

DETAILED DESCRIPTION OF THE INVENTION

This invention provides a composition which adheres to an area of the skin or mucosa, and delivers pharmaceutical agent or a combination of agents to produce a local or systemic effect over a prolonged period of time.

In accordance with one embodiment of the present invention, a local anesthetic substantially in solution with a solvent for the anesthetic in admixture with a finite, flexible, pharmaceutically acceptable adhesive carrier which is preferably a bioadhesive, is provided for topical application to the skin or dermal membrane of a mammal.

In accordance with a further embodiment of the present invention, a combination of local anesthetic agents, a solvent for the anesthetic agents and a flexible, preferably adhesive pharmaceutically acceptable adhesive carrier is provided for topical application to the skin or mucosa of a mammal.

The anesthetic agents of this invention are those known, or of a type known, in the art. The local anesthetic bases encompassed by this invention are weak organic bases which are lipophilic in nature and thus poorly soluble in water. However, these bases will react with organic or inorganic acids to form acidic, water soluble acid addition salts. Thus, the term "base" as used herein means the un-ionized form of the anesthetic that can furnish an electron pair to form a covalent bond. The term "acid" as used herein is a substance that can take up an electron pair to form a covalent bond. The term "salt" as used herein means the form produced by a base, for example an anesthetic base, upon its reaction with an organic or inorganic acid.

The base form and the salt form of the anesthetic agent incorporated in the present combination composition must be different anesthetic agents to achieve maximum duration of the combined anesthetic effect. By the term "different" is meant that the salt form in any combination is not a salt of the base form used in the given combination.

Local anesthetic agents suitable for use in the practice of this invention include amides and esters. Examples of the amides are lidocaine, prilocaine, mepivacaine, bupivacaine, dibucaine and etidocaine. Esters include procaine, tetracaine, propoxycaine, chloroprocaine, benzocaine, butamben picrate, cocaine, hexylcaine, piperocaine, oxyprocaine and proparacaine. Other suitable local anesthetics for use in the practice of this invention include cyclomethycaine, dimethisoquin, ketocaine, diperodon, dyclonine and pramoxine, all typically administered in the form of the acid addition hydrochloride or sulfate salts.

The acid-addition salts of the present invention are any non-toxic, pharmaceutically acceptable organic or inorganic salts. Typical inorganic salts are the hydrogen halides, especially the hydrochlorides, carbonates, borates, phosphates, sulfates, hydrogen sulfates, hydrobromides, nitrates, sulfides, and arsenates. Typical organic salts are salts of mono- and polycarboxylic acids such as the citrate, tartrate, malate, cinnamate, oxalate, formate, succinate and phthalates.

The solvents for the anesthetic agents are non-toxic, pharmaceutically acceptable substances, preferably liquids, which do not substantially negatively affect the adhesion properties of the system. The solvent is preferably a polyhydric alcohol or combination of polyhydric alcohols. The term polyhydric alcohol means any organic polyalcohol and includes dipropylene glycol, propylene glycol, polyethylene glycol, glycerin, butylene glycol, hexylene glycol, polyoxyethylene, polypropylene glycol, sorbitol, ethylene glycol, and the like. Other suitable solvents include fatty acids such as oleic acid, linoleic acid, capric acid and the like, as well as fatty esters or alcohols. Further suitable solvents include other non-toxic, non-volatile solvents commonly used in dermal or transdermal compositions for dissolving like compounds.

The above mentioned polyhydric alcohols may include those having 2 to 6 alcoholic hydroxyl groups. Such polyhydric alcohols include glycols, triols and polyols having 4 to 6 alcoholic hydroxyl groups. Typical of said glycols are glycols containing 2 to 6 carbon atoms, e.g. ethylene glycol, propylene glycol, butylene glycol, polyethylene glycol (average molecular weight about 200–8,000, preferably about 200 to 6,000), etc. Examples of said triols include glycerin, trimethylolpropane, etc. Said polyols are exemplified by sorbitol (sorbit), polyvinylpyrrolidone, etc. These polyhydric alcohols may be used either singly or in combination (preferably, of two or three). Thus, for example, glycerin alone or a mixture of glycerin and butylene glycol is employed.

Among those polyhydric alcohols, those which satisfy the requirements relevant to the adjustment and maintenance of softness of the external drug of the invention, the compatibility or co-dispersibility with the other components, and provide a proper consistency of the composition, may be freely used. Those which are low in volatility and plastic, are generally preferred and, in this regard, dipropylene glycol, glycerin, propylene glycol, butylene glycol, and sorbitol are appropriate solvents, according to the invention.

Although the exact amount of the polyhydric alcohols in the composition depends on the nature of other components, and therefore cannot be stated in general terms, the proportion may range from about 5 to about 70 weight percent based on the whole composition.

The high concentrations of microdispersed anesthetic agent of this invention are achieved typically by mixing the anesthetic agents with the solvent, preferably at an elevated temperature, for example about 70° to 100° C., to obtain a mixture, preferably a solution, of the anesthetic agents which is then added to the pharmaceutically acceptable adhesive carrier. The term "microdispersed" is intended to mean that in the solvent, and subsequently the carrier, there is an intimate dispersion of the anesthetic agent at the molecular or ionic level, such that crystals of the anesthetic agent cannot be detected using a microscope having a magnification of 25×.

Preferably the anesthetic agent is substantially dissolved in the solvent so that when mixed with the adhesive, the anesthetic is microdispersed in the composition.

Solvent selection for a single anesthetic agent or a combination of anesthetic agents in either the free base form or in the acid-addition salt form, depends on the form of the anesthetic agent, namely whether it is in free base form or acid-addition salt form. Solvents for the salt form of anesthetic agent are polar organic solvents. Polar organic solvents are preferably polyhydric alcohols, as discussed above. Various other solvents suitable for either the base or acid-addition form of the anesthetic agent are those solvents known to dissolve either or both of these two types of forms including cyclic ketones such as 2-pyrrolidone; N-(2-hydroxyethyl) pyrrolidone, N-methylpyrrolidone, 1-dodecylazacycloheptan2-one and other n-substituted alkyl-azacycloalkyl-2-ones (azones) dimethylformadide, and dimethylsulfoxide. Other suitable solvents for the free base form of the anesthetic agent are cell envelope disordering compounds known to be useful in topical pharmaceutical preparation, which compounds are thought to assist in skin penetration by disordering the lipid structure of the stratum corneum cell-envelopes. Some of these compounds are generally encompassed by the formula:

R-X wherein R is a straight-chain alkyl of about 7 to 16 carbon atoms, a non-terminal alkenyl of about 7 to 22 carbon atoms, or a branched-chain alkyl of from about 13 to 22 carbon atoms, and X is —OH, —COOCH$_3$, —COOC$_2$H$_5$, —OCOCH$_3$, —SOCH$_3$, —P(CH$_3$)$_2$O, —COOCH$_2$H$_4$OC$_2$H$_4$OH, —COOCH(CHOH)$_4$C-H$_2$OH, —COOCH$_2$CHOHCH3, —COOCH$_2$C-H(OR")CH$_2$OR". —(OCH$_2$CH$_2$)$_m$OH, —COOR', or —CONR'$_2$
where R; is —H, —CH$_3$, —C$_2$H$_5$, —C$_3$H$_7$ OR —C$_2$-H$_4$OH; R" is —H, or a non-terminal alkenyl of about 7 to 22 carbon atoms; and m is a positive integer from 2 to 6; provided that when R" is an alkenyl and X is —OH or —COOH, at least one double bond is in the cis-configuration.

It has been discovered that high concentrations of a combination of microdispersed anesthetic agents, namely up to 50% by weight of the finite, flexible composition, require the use of a solvent as herein described. Omission of the solvent in the procedure of Example 1 below yields a product filled with crystals or crystalline mass.

In particularly preferred embodiments of this invention, the free base local anesthetic agent is selected from the group comprising lidocaine, procaine, propoxycaine, mepivacaine, prilocaine, dyclonine, pramoxine, benzocaine and chloroprocaine. The salt form is preferably one selected from the group comprising prilocaine, tetracaine, bupivacaine, dyclonine, dibucaine, etidocaine and lidocaine salts. The aforementioned bases and salts can be used alone or in combination with other anesthetic bases and salts as needed to achieve therapeutically affective levels when administered transdermally.

The term "therapeutically effective amount" is intended to mean the amount of drug sufficient to produce an anesthetic effect when applied topically. These amounts are known in the art or may be determined by methods known in the art, and typically range from about 1 to 20,000 mg per human adult and preferably about 10 to 10,000 mg and most preferably range from about 20 to 5,000 mg of the anesthetic agent per application, depending upon the anesthetic agents chosen, and whether the skin or mucous membrane is the site of action. The only upper limit on the amount of anesthetic in the composition is that the preparation is substantially free of crystals of anesthetic agent and the amount of solvent used is not sufficient to undesirably affect the adhesive properties of the whole composition. Thus, the single ingredient anesthetic agent contains a therapeutically effective amount of anesthetic agent within the foregoing range.

The concentration as well as the quantity of anesthetic per square centimeter can be varied independently in order to achieve the desired effect. Higher concentrations of anesthetic base contained in a dosage form of decreased thickness will result in a anesthetic with fast onset and short duration. High concentrations of the anesthetic base contained in a dosage form of increased thickness (higher mg of anesthetic per square centimeter) will result in potent anesthesia with fast onset and long duration. Low concentrations of the anesthetic base in a dosage form of decreased thickness will result in mild anesthesia with longer onset and short duration. Low concentrations of the anesthetic base, contained in a dosage form of increased thickness will have mild anesthesia with longer onset and longer duration. As shown in the above explanation, the ability to vary the concentration of anesthetic from very low (about 1%) to high (40% or higher) of the total composition, when combined with the ability to coat thin (about 0.001 inches) or thick (about 0.500 or more inches) enables the practitioner of the invention to vary the dosage of the system as needed for particular anatomical sites of interest.

As a general rule, in the case of mucosal application, the anesthetic drug selected, the concentration and thickness and the duration of the application is determined based upon the anesthetic's ability to penetrate the mucosa and to be at peak effectiveness within about 2 to 30 minutes. The duration of the effect of the anesthetic on the oral mucosa should range between about 2 to 240 minutes, depending on the anesthetic agent selected, the concentration of the anesthetic and the thickness of application. Longer or shorter durations can also be selected dependent on need, as will be apparent to one skilled in the art.

The ratio of the free base form to the salt form in the composition of this invention will depend on several factors, namely: (1) the identity of the salt and base used; (2) the desired duration of action; and (3) the desired rapidity of anesthetic effect. As a general rule in the case of mucosal application, the ratios of base to salt are such that the free base form preferably should penetrate the mucosa and be at its peak effectiveness within about a 2 to 30 minute period, whereas, the salt form should preferably penetrate the mucosa and be at its peak effectiveness within a period of about 10 to 75 minutes. The duration of the effect of these on the oral mucosa will range between about 2 to 240 minutes depending on the base/salt combination selected and the length of application time.

The term "onset of anesthesia" is intended to mean the time to peak effect on the individual nerves. Onset of anesthesia principally depends upon the lipid solubility, molecular size, and quantity of available, unionized form of the local anesthetic. Thus, anesthetics with a high lipid solubility or a low $pK_a$, or both, have a more rapid onset of anesthesia.

The term "duration of anesthesia" as used herein means the period of time during which the local anesthetic measurably blocks nerve conduction. The foregoing depends upon all of the factors listed for onset of anesthesia, as well as on the extent of protein binding of the anesthetic agent.

The anesthetic agent free base can penetrate intact skin to a limited degree, and will more rapidly penetrate the skin if the keratin layers are abraded. In the case of the oral mucosa, the anesthetic base will penetrate much more readily due to the different keratin composition and the resulting difference in the hydrophilicity as compared to the stratum corneum of intact skin.

As a general rule, the salt forms of the aforementioned anesthetics do not appreciably penetrate intact skin, but the un-ionized base form do penetrate to a limited degree. Both forms, salt and base, will penetrate abraded keratin layers. The salt as well as the base will penetrate, to a differing degree, the buccal mucosa due to the buccal mucosa's hydrophilicity, as compared to the stratum corneum of intact skin. Generally, the higher the lipid content of the mucosal membrane, the more rapidly the base form of the anesthetic agent will be absorbed. Therefore, when the composition is used for application to oral or buccal mucosa, the different lipid contents of the gum (gingiva) and the alveolar mucosa must be kept in mind in order to obtain the optimal penetration rate.

Although applicants do not intend to be bound by any theory or proposed mechanism of operation, it is believed that the base which is lipid soluble has a rapid onset of anesthesia since it enters the lipo-protein nerve membrane preventing the depolarization and ion exchange involved in stimulus conduction. On the other hand, the salt which is not lipid soluble, penetrates to the lipo-protein nerve membrane only after the buffering capacity of the skin or mucosal tissue converts the salt to the base, the final result being a delayed onset of anesthesia.

The salts of this invention are selected on the basis of onset of anesthesia and duration of anesthesia. Adjusting the ratio of base to salt affects the relative onset as well as the duration of anesthetic action. The greater the amount of anesthetic agent having a rapid onset of action, the shorter the onset of anesthesia. Similarly, the greater the amount of the anesthetic agent having a prolonged duration of anesthesia, the more prolonged the duration of anesthesia. More than two anesthetic agents may be used to have a broader spectrum of activity. Moreover, the composition can include other drugs used concomitantly.

Generally, the concentration of solubilized anesthetic agent can range, on a weight basis, between about 1 and about 50%, preferably between 2.5 and 40% and more preferably between 5 and 30% of the total weight of the composition. In a preferred embodiment of the invention, the concentration of dissolved base is 20% by weight of the total composition. The base used in the preferred embodiment for a single ingredient preparation is lidocaine.

Generally, for the hydrochloride salts the ratio by weight of base to salt is about 90:10 to about 60:40, preferably about 75:25 to about 60:40, and more preferably about 70:30 to about 60:40. For other salts, the ratios are comparable based on relative molar amounts. In a preferred embodiment of the invention, the ratio is about 2:1 base to salt, respectively. The base used in the preferred embodiment is lidocaine and the preferred salt is a salt of prilocaine, bupivacaine, dyclonine, mepivacaine, or tetracaine, preferably the hydrochloride salt.

Table 1 below summarizes the peak and duration of action of selected local anesthetics based primarily on application to skin or mucous membranes:

TABLE 1

| Local Anesthetic | Minimum Adult Dose | Maximum Adult Dose (mg) | Peak Effect (minutes) | Duration of Effect (minutes) |
|---|---|---|---|---|
| Dibucaine | | 25 | <15 | 120–240 |
| Lidocaine | | 750 | 2–5 | 30–60 |
| Benzocaine | | 5000 | 1 | 30–60 |
| Cocaine | | 50 | 2–5 | 30–120 |
| Tetracaine | | 50 | 3–8 | 30–60 |
| Dyclonine | | 100 | <10 | <60 |
| Pramoxine | | 200 | 3–5 | NA |

NA: Not Available.
Source: Drug Facts and Comparisons, 1990 edition, J. B. Lippincott Company, St. Louis, MO. Page 601.

In general, the relative speed of onset of anesthesia and duration of anesthesia for any given form of anesthetic agent is available in the literature or can be calculated by standard tests.

Onset time, as well as duration of anesthesia, will vary from individual to individual as well as on the basis of the site of application. When applying the composition to highly keratinized dermal tissues, the onset of anesthesia may take as long as 2 to 4 hours.

The composition of this invention can be manufactured by numerous methods known in the art which permit the achievement of a microdispersed anesthetic agent, including extruding, molding, solvent casting, coating, and all other methods which employ a solvent to disperse the drug in a carrier prior to shaping of the carrier.

Contrary to the typical method for manufacturing a drug in a solvent containing adhesive, the preparation is either not dried so as to force removal of the solvent from the adhesive or a solvent is used which is not substantially evaporated during the conditions of manufacture. The composition in question can then be applied to a flexible backing or a combination of backings which will serve to define the size and shape of a single dosage of the composition. Such backing may be a three dimensional material such as paper, a non-woven fabric or natural or synthetic polymer substance. Methods of coating backings are well-known in the art and include techniques involving Mayer rod, gravure, and knife-over roll. Further processing of backings may involve the use of converting equipment for die cutting.

The finished dosage form will be substantially occlusive to water permeation in in-vivo.

For example, the anesthetic agents are dissolved in a solvent, preferably a polyhydric alcohol, and then the resulting mixture is added to an adhesive prior to being placed onto the flexible form or backing. The final form in which the composition of the invention will be applied depends upon the anatomical site of application.

The phrase "flexible, finite, pharmaceutically acceptable carrier" is intended to mean a solid capable of conforming to a surface with which it comes into contact and which is capable of maintaining the contact so as to facilitate topical application without any adverse physiological response, and which can be used to establish the compositions herein in their preferred solid form without being appreciably decomposed by aqueous contact during administration to a patient.

An important characteristic of the present invention relates to the substantially water-free and water-insoluble nature of the composition. By the term "substantially water-free" is meant that the preparation contains less than about 10% by weight water, and preferably less than 5%, and most preferably less than 3%. In general, it is desirable to avoid the addition of water entirely and to eliminate, as far as possible, the presence of water in the other ingredients of the composition. By the term "substantially water insoluble" is meant that the composition remains "finite" and does not generally detach from the skin or other dermal membrane at the site of application and under the conditions of regular, intended use for a period of at least 3 hours. The advantages to be derived from the substantially water-free and water-insoluble nature of the compositions of the present invention include achievement of higher concentrations of drug. Another advantage of these compositions is minimization of precipitation of drug, which precipitation affects processing of the composition, affects rate of delivery of the drugs and in certain cases can affect sensitivity of the subject to be treated to the drug.

Suitable adhesive carriers include any of the nontoxic polymers, particularly those of the type used to carry drugs for transdermal delivery including natural or synthetic elastomers, such as polyisobutylene, styrene, butadiene, styrene isoprene block copolymers, acrylics, urethanes, silicones, styrene butadiene copolymers, methyl acrylate copolymers, acrylic acid, polyacrylates, and polysacchrides such as, karaya gum, tragacanth gum, pectin, guar gum, cellulose, and cellulose derivatives such as methyl cellulose, propyl cellulose, cellulose acetate and the like, along with other substances known for use in transdermal preparations capable of forming a solid colloid that can adhere to skin and mucosa, used alone or in combination with other suitable carriers. A particularly preferred carrier is a bioadhesive for application to the dermis, preferably the mucosa.

The adhesive can be modified so as to adhere to the skin or mucosal tissue, depending on the intended application site. As stated above, preferred adhesives for application to the skin are bioadhesives.

The term "adhesive" as used herein means a substance, inorganic or organic, natural or synthetic, that is capable of surface attachment to the intended application site.

The term "bioadhesive" as used herein means an adhesive which attaches and preferably strongly attaches to a live or freshly killed biological surface such as skin or mucosal tissue upon hydration. Indeed, to qualify as a bioadhesive, a substance must be capable of maintaining adhesion in moist or wet in in vivo or in vitro environments.

The strength of adherence can be measured by standard tests for measuring the force, e.g. in dynes per square centimeter, as disclosed in U.S. Pat. No. 4,615,697. Suitable bioadhesives include those prepared from optionally partially esterified polyacrylic acid polymers, including but not limited to, polyacrylic acid polymers lightly crosslinked with a polyalkenyl polyether such as those commercially available from B. F. Goodrich, Cincinnati, Ohio, under the trademarks Carbopol 934, 934P, 940 and 941.

Other suitable bioadhesives include natural or synthetic polysacchardies. The term "polysaccharide" as used herein means a carbohydrate decomposable by hydrolysis into two or more molecules of monosaccharides or their derivatives. Suitable polysaccharides include cellulose derivatives such as methylcellulose, cellulose acetate, carboxymethylcellulose, hydroxyethylcellulose and the like. Other suitable bioadhesives are pectin, a mixture of sulfated sucrose and aluminum hydroxide, hydrophilic polysaccharide gums such as natural plant exudates, including karaya gum, ghatti gum, tragacanth gum, xanthan gum, jaraya gum and the like, as well as seed gums such as guar gum, locust bean gum, psillium seed gum and the like.

In addition to the above ingredients, there may also be incorporated other additives selected from among the various pharmaceutically acceptable additives available to those skilled in the art. These additives include binders, stabilizers, preservatives, flavorings and pigments.

The composition is administered in appropriate sizes, typically having a surface area of from about 0.1 to about 200 cm$^2$ or conveniently 0 2 to 100 cm$^2$. The anesthetic agent is loaded into the composition in as high a concentration as necessary to effect therapy, e.g., in a range from about 0.1 mg/cm$^2$ to about 50 or more mg/cm$^2$.

In general, the composition can have the following types and amounts of ingredients:

| Ingredient | Typical Range (% by weight) | Preferred Range (% by weight) | Optimum Range (% by weight) |
| --- | --- | --- | --- |
| Adhesive | 15 to 60 | 20 to 50 | 20 to 35 |
| Solvent | 2 to 75 | 5 to 70 | 20 to 40 |
| Anesthetic agent (single ingredient) | 1 to 50 | 5 to 40 | 10 to 30 |
| Anesthetic agent (multiple ingredient) | 1 to 50 | 5 to 40 | 10 to 30 |
| Anesthetic base | .7 to 50 | 5 to 40 | 7 to 20 |
| Anesthetic salt | .3 to 25 | 2 to 30 | 3 to 20 |

In one embodiment, the composition of the invention comprises:
  a. a therapeutically effective amount of at least one local anesthetic;
  b. a pharmaceutically acceptable solvent for the anesthetic, in an amount from about 5 to about 70 weight percent based on the weight of the whole composition;
  c. in admixture with the anesthetic agent in the solvent, a flexible, finite, pharmaceutically acceptable polysaccharide bioadhesive carrier in an amount from about 20 to about 50 weight percent based on the weight of the whole composition;
wherein said composition is substantially free of water and is substantially water insoluble.

In another embodiment, the composition of the invention comprises:
  a. a therapeutically effective amount of a first local anesthetic agent in base form;
  b. a therapeutically effective amount of a different, second local anesthetic agent in salt form;
  c. a solvent for the first and second local anesthetic agents in an amount from about 5 to about 70 weight percent based on the weight of the whole composition; and d. in an admixture with the anesthetic agents in the solvent, a flexible, finite, pharmaceutically acceptable, adhesive carrier in an amount from about 20 to about 50 weight percent based on the weight of the whole composition;

wherein the composition is substantially free of water and is substantially water insoluble.

Another embodiment of the invention relates to a method of administering one or more local anesthetics to a subject in need of such local anesthetic. The term "administering" is intended to mean any mode of application which results in the physical contact of the composition with an anatomical site in need of anesthesia. The term "subject" is intended to include all warm-blooded mammals, preferably humans.

The following examples will further describe the instant invention, and are used for the purposes of illustration only, and should not be considered as limiting in any way the invention being disclosed herein. Percent (%) as used in these examples refer to percentage of the liquid formulation on a weight to weight basis and temperatures are given in degrees celsius (°C).

EXAMPLE 1

| Ingredient | % (w/w) |
| --- | --- |
| Adhesive (karaya gum) | 21 |
| Binder (lecithin) | 11 |
| Solvent (propylene glycol) | 7 |
| Solvent (glycerin) | 19 |
| Anesthetic agent base (lidocaine base) | 28 |
| Anesthetic agent salt (prilocaine hydrochloride) | 14 |

The final product is manufactured by first blending the lidocaine base, prilocaine hydrochloride, propylene glycol, lecithin and glycerin at about 70° to 90° C. until all of the drug is dissolved. The solution is then cooled to 20° to 35° C. prior to adding the karaya gum. Once the karaya gum is added, the final composition is applied to a suitable backing material such as a non-woven, polyester film (for example, the film sold under the trademark Sontara 8100, manufactured by DuPont de Nemours, E. I. and Co., Wilmington, Del.) and warmed to about 100° C. to accelerate the formation of the gel into its final, finite form.

EXAMPLE 2

| Ingredient | % (w/w) |
| --- | --- |
| Adhesive (karaya gum) | 30 |
| Solvent (glycerin) | 30 |
| Solvent (propylene glycol) | 39 |
| Anesthetic agent base (lidocaine base) | 0.7 |
| Anesthetic agent salt (prilocaine hydrochloride) | 0.3 |

The procedure set forth in Example 1 is used with appropriate substitutions of quantities to prepare this formulation.

EXAMPLE 3

| Ingredient | % (w/w) |
| --- | --- |
| Adhesive (karaya gum) | 21 |
| Binder (lecithin) | 4 |
| Solvent (propylene glycol) | 3 |
| Solvent (isocetyl alcohol) | 7 |
| Solvent (glycerin) | 26 |
| Anesthetic agent base (lidocaine base) | 26 |

| Ingredient | % (w/w) |
| --- | --- |
| Anesthetic agent salt (tetracaine hydrochloride) | 13 |

The procedure of Example 1 is used with appropriate substitution of ingredients to prepare this formulation.

EXAMPLE 4

| Ingredient | % (w/w) |
| --- | --- |
| Adhesive (karaya gum) | 27 |
| Solvent (propylene glycol) | 29 |
| Solvent (glycerin) | 4 |
| Anesthetic agent base (lidocaine base) | 28 |
| Anesthetic agent salt (dyclonine hydrochloride) | 12 |

The procedure of Example 1 is used with appropriate substitution of ingredients to prepare this formulation.

EXAMPLE 5

| Ingredient | % (w/w) |
| --- | --- |
| Adhesive (karaya gum) | 26 |
| Binder (lecithin) | 10 |
| Solvent (propylene glycol) | 7 |
| Solvent (butylene glycol) | 17 |
| Solvent (glycerin) | 10 |
| Anesthetic agent base (lidocaine base) | 20 |
| Anesthetic agent salt (dyclonine hydrochloride) | 10 |

The procedure of Example 1 is used with appropriate substitution of ingredients to prepare this formulation.

EXAMPLE 6

| Ingredient | % (w/w) |
| --- | --- |
| Adhesive (karaya gum) | 27 |
| Binder (lecithin) | 12 |
| Solvent (propylene glycol) | 8 |
| Solvent (glycerin) | 13 |
| Anesthetic agent base (lidocaine base) | 27 |
| Anesthetic agent salt (bupivacaine hydrochloride) | 13 |

The procedure of Example 1 is used with appropriate substitution of ingredients to prepare this formulation.

EXAMPLE 7

| Ingredient | % (w/w) |
| --- | --- |
| Adhesive (karaya gum) | 27 |
| Binder (lecithin) | 12 |
| Solvent (propylene glycol) | 8 |
| Solvent (glycerin) | 13 |
| Anesthetic agent base (lidocaine base) | 13 |
| Anesthetic agent salt (bupivacaine hydrochloride) | 27 |

The procedure of Example 1 is used with appropriate substitution of ingredients to prepare this formulation.

EXAMPLE 8

| Ingredient | % (w/w) |
| --- | --- |
| Adhesive (karaya gum) | 21 |
| Binder (lecithin) | 11 |
| Solvent (propylene glycol) | 7 |
| Solvent (glycerin) | 19 |
| Anesthetic agent base (lidocaine base) | 28 |

| Ingredient | % (w/w) |
|---|---|
| Anesthetic agent salt (mepivacaine hydrochloride) | 14 |

The procedure of Example 1 is used with appropriate substitution of ingredients to prepare this formulation.

EXAMPLE 9

| Ingredient | % (w/w) |
|---|---|
| Adhesive (Carbopol 934P, a polycarboxylic acid sold by B. F. Goodrich Chemical Company) | 20 |
| Solvent (propylene glycol) | 15 |
| Solvent (glycerin) | 20 |
| Anesthetic agent base (lidocaine base) | 30 |
| Anesthetic agent salt (bupivacaine hydrochloride) | 15 |

The procedure of Example 1 is used with appropriate substitution of ingredients to prepare this formulation.

EXAMPLE 10

| Ingredient | % (w/w) |
|---|---|
| Adhesive (karaya gum) | 24 |
| Solvent (propylene glycol) | 3 |
| Adhesive (glycerin) | 14 |
| Solvent (isocetyl alcohol) | 7 |
| Binder (lecithin) | 4 |
| Anesthetic agent base (lidocaine base) | 32 |
| Anesthetic agent salt (tetracaine hydrochloride) | 16 |

The above formulation is prepared by a procedure which is analogous to that set forth in Example 1.

The addition of up to 2% by weight water in this formulation did not result in precipitation of the anesthetic agent(s) prior to addition of the karaya gum. The addition of 3% to 10% water results in increased precipitation, which at 10% water results in a crystalline mass.

EXAMPLE 11

| Ingredient | % (w/w) |
|---|---|
| Adhesive (tragacanth gum) | 24 |
| Adhesive (pectin) | 5 |
| Solvent (propylene glycol) | 12 |
| Solvent (glycerin) | 12 |
| Anesthetic agent base (mepivacaine base) | 35 |
| Anesthetic agent salt (lidocaine hydrochloride) | 12 |

The above formulation is prepared by a procedure analogous to that of Example 1

EXAMPLE 12

| Ingredient | % (w/w) |
|---|---|
| Bioadhesive (karaya gum) | 33 |
| Binder (lecithin) | 9 |
| Solvent (propylene glycol) | 6 |
| Solvent (dipropylene glycol) | 15 |
| Solvent (glycerin) | 17 |
| Anesthetic agent base (lidocaine base) | 20 |

The final product is manufactured by first blending the lidocaine base, lecithin, propylene glycol, dipropylene glycol and glycerine at about 70° to 90° C. until all of the drug is dissolved. The solution is then chilled to about 20° to 40° C. prior to adding the karaya gum. Once the karaya gum is added, the final composition is applied to a suitable backing material such as a nonwoven polyester film (for example the film sold under the trademark Sonata 8100 manufactured by DuPont de Nemours, E. I. and Co., Wilmington, Del.) and warned at about 708° to 130° C. to accelerate the formation of the gel into its final solid form. This gel can be directly applied to the oral mucosa or overlaid with a skin contact adhesive for skin adhesion.

EXAMPLE 13

| Ingredient | % (w/w) |
|---|---|
| Bioadhesive (karaya gum) | 33 |
| Binder (lecithin) | 5 |
| Solvent (propylene glycol) | 7 |
| Solvent (dipropylene glycol) | 12 |
| Solvent (glycerin) | 33 |
| Anesthetic agent base (lidocaine base) | 10 |

The procedure of Example 12 is used with appropriate substitution of ingredients to prepare this formulation.

EXAMPLE 14

| Ingredient | % (w/w) |
|---|---|
| Bioadhesive (karaya gum) | 35 |
| Binder (lecithin) | 5 |
| Solvent (propylene glycol) | 7 |
| Solvent (dipropylene glycol) | 12 |
| Solvent (glycerin) | 36 |
| Anesthetic agent base (lidocaine base) | 5 |

The procedure of Example 12 is used with appropriate substitution of ingredients to prepare this formulation.

EXAMPLE 15

| Ingredient | % (w/w) |
|---|---|
| Bioadhesive (karaya gum) | 30 |
| Binder (lecithin) | 9 |
| Solvent (propylene glycol) | 6 |
| Solvent (dipropylene glycol) | 15 |
| Solvent (glycerin) | 15 |
| Anesthetic agent base (lidocaine base) | 25 |

The procedure of Example 12 is used with appropriate substitution of ingredients to prepare this formulation.

EXAMPLE 16

| Ingredient | % (w/w) |
|---|---|
| Bioadhesive (karaya gum) | 20 |
| Binder (lecithin) | 9 |
| Solvent (propylene glycol) | 6 |
| Solvent (dipropylene glycol) | 10 |
| Solvent (glycerin) | 10 |
| Solvent (benzyl alcohol) | 5 |
| Anesthetic agent base (lidocaine base) | 40 |

The procedure of Example 12 is used with appropriate substitution of ingredients to prepare this formulation.

EXAMPLE 17

| Ingredient | % (w/w) |
| --- | --- |
| Bioadhesive (karaya gum) | 25 |
| Binder (lecithin) | 8 |
| Solvent (isocetyl alcohol) | 5 |
| Solvent (propylene glycol) | 12 |
| Solvent (glycerin) | 10 |
| Anesthetic agent base (prilocaine base) | 40 |

The procedure of Example 12 is used with appropriate substitution of ingredients to prepare this formulation.

EXAMPLE 18

| Ingredient | % (w/w) |
| --- | --- |
| Bioadhesive (karaya gum) | 25 |
| Binder (lecithin) | 4 |
| Solvent (propylene glycol) | 6 |
| Solvent (benzyl alcohol) | 10 |
| Solvent (dipropylene glycol) | 10 |
| Solvent (glycerin) | 5 |
| Anesthetic agent base (tetracaine base) | 40 |

The procedure of Example 12 is used with appropriate substitution of ingredients to prepare this formulation.

EXAMPLE 19

| Ingredient | % (w/w) |
| --- | --- |
| Bioadhesive (karaya gum) | 30 |
| Binder (lecithin) | 8 |
| Solvent (propylene glycol) | 12 |
| Solvent (dipropylene glycol) | 25 |
| Solvent (benzyl alcohol) | 5 |
| Solvent (glycerin) | 10 |
| Anesthetic agent base (dibucaine base) | 10 |

The procedure of Example 12 is used with appropriate substitution of ingredients to prepare this formulation.

EXAMPLE 20

| Ingredient | % (w/w) |
| --- | --- |
| Bioadhesive (karaya gum) | 28 |
| Bioadhesive (carbopol 934) | 2 |
| Solvent (propylene glycol) | 6 |
| Solvent (dipropylene glycol) | 15 |
| Solvent (glycerin) | 15 |
| Binder (lecithin) | 9 |
| Anesthetic agent base (lidocaine base) | 25 |

The procedure of Example 12 is used with appropriate substitution of ingredients to prepare this formulation. The only difference is that the carbopol 934 is added to the original blend prior to heating it.

EXAMPLE 21

| Ingredient | % (w/w) |
| --- | --- |
| Bioadhesive (tragacanth gum) | 27 |
| Bioadhesive (pectin) | 6 |
| Binder (lecithin) | 9 |
| Solvent (propylene glycol) | 6 |
| Solvent (dipropylene glycol) | 15 |
| Solvent (glycerin) | 17 |
| Anesthetic agent base (lidocaine base) | 20 |

The procedure of Example 12 is used with the solvents and anesthetic agent base added in the initial step followed later by the adhesives addition.

EXAMPLE 22

| Ingredient | % (w/w) |
| --- | --- |
| Bioadhesive (cellulose acetate) | 27 |
| Solvent (dipropylene glycol) | 43 |
| Anesthetic agent base (prilocaine base) | 20 |

This formulation is prepared according to the procedure which is analogous to the procedure set forth in Example 1.

EXAMPLE 23

| Ingredient | % (w/w) |
| --- | --- |
| Bioadhesive (Xanthan gum) | 27 |
| Bioadhesive (Pectin) | 6 |
| Binder (lecithin) | 9 |
| Solvent (propylene glycol) | 6 |
| Solvent (dipropylene glycol) | 15 |
| Solvent (glycerin) | 17 |
| Anesthetic agent base (lidocaine base) | 20 |

The procedure of Example 12 is followed with the appropriate substitution of ingredients.

The foregoing examples are illustrative embodiments of the invention and are merely exemplary. A person skilled in the art may make variations and modification without departing from the spirit and scope of the invention. All such modifications and variations are intended to be included within the scope of the invention as described in this specification and the appended claims.

Indeed, the present invention is intended to encompass and be suitable for any of the following drugs as the pharmaceutically active agent in the composition:

1. Analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like;

2. Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cydobarbital, codeine, lidocaine, tetracaine, dyclonine, dibucaine, cocaine, procaine, mepivacaine, bupivacaine, etidocaine, prilocaine, benzocaine, fentanyl, nicotine, and the like;

3. Antihistaminics or antiallergic agents such as, diphenhydramine, dimenhydrinate, perphenazine, tripolidine, pyrilamine, chlorcyclizine, promethazine, carbinoxamine, tripelennamine, brompheniramine, hydroxyzine, cyclizine, meclizine, clorprenaline, terfenadine, chlorpheniramine, and the like;

4. Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like;

5. Steroids such as, androgenic steriods, such as, testosterone, methyltestosterone, fluoxymesterone, estrogens such as, conjugated estrogens, esterified estrogens, estropipate, 17-$\beta$ estradiol, 17-$\beta$ estradiol valerate, equilin, mestranol, estrone, estriol, 17-$\beta$ ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-$\alpha$ hydroxyprogesterone, dydrogesterone, dimethisterone, ethinylestrenol, norgestrel, demegestone, promegestone, megestrol acetate, and the like;

6. Respiratory agents such as, theophilline and $\beta_2$-adrenergic agonists, such as, albuterol, terbutaline, metaproterenol, ritodrine, carbuterol, fenoterol, quinterenol, rimiterol, solmefamol, soterenol, tetroquinol, and the like;

7. Sympathomimetics such as, dopamine, norepinephrine, phenylpropanolamine, phenylephrine, pseudoephedrine, amphetamine, propylhexedrine, arecoline, and the like;

8. local anesthetics such as, benzocaine, procaine, dibucaine, lidocaine, and the like;

9. Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides; nitrofrantoin, nystatin, amphotericin, fradiomycin, sulfonamides, purrolnitrin, clotrimazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like;

10. Antihypertensive agents such as, clonidine, $\alpha$-methyldopa, reserpine, syrosingopine, rescinnamine, cinnarizine, hydrazine, prazosin, and the like;

11. Antihypertensive diuretics such as, chlorothiazide, hydrochlorothrazide, bendoflumethazide, trichlormethiazide, furosemide, tripamide, methylclothiazide, penfluzide, hydrothiazide, spironolactone, metolazone, and the like;

12. Cardiotonics such as, digitalis, ubidecarenone, dopamine, and the like;

13. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like;

14. Vasoconstrictors such as, dihydroergotamine, dihydroergotoxine, and the like;

15. $\beta$-blockers or antiarrhythmic agents such as, timolol pindolol, propranolol, and the like;

16. Calcium antagonists and other circulatory organ agents, such as, aptopril, diltiazem, nifedipine, nicardipine, verapamil, bencyclane, ifenprodil tartarate, molsidomine, clonidine, prazosin, and the like;

17. Anti-convulstants such as, nitrazepam, meprobamate, phenytoin, and the like;

18. Agents for dizziness such as, isoprenaline, betahistine, scopolamine, and the like;

19. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like;

20. Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranqulizers such as, chlorprathixene, thiothixene, haloperidol, bromperidol, loxapine, and molindone, as well as, those agents used at lower doses in the treatment of nausea, vomiting, and the like;

21. Muscle relaxants such as, tolperisone, baclofen, dantrolene sodium, cyclobenzaprine;

22. Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like;

23. Respiratory agents such as, codeine, ephedrine, isoproterenol, dextromethorphan, orciprenaline, ipratropium bromide, cromglycic acid, and the like;

24 Non-steroidal hormones or antihormones such as, corticotropin, oxytocin, vasopressin, salivary hormone, thyroid hormone, adrenal hormone, kallikrein, insulin, oxendolone, and the like;

25. Vitamins such as, vitamins A, B, C, D, E and K and derivatives thereof, calciferols, mecobalamin, and the like for dermatologically use;

26. Antitumor agents such as, 5-fluorouracil and derivatives thereof, krestin, picibanil, ancitabine, cytarabine, and the like;

27. Enzymes such as, lysozyme, urokinaze, and the like;

28. Herb medicines or crude extracts such as, glycyrrhiza, aloe, Sikon (Lithospermi Radix), and the like;

29. Miotics such as pilocarpine, and the like; lo 30. Cholinergic agonists such as, choline, acetylcholine, methacholine, carbachol, bethanechol, pilocarpine, muscarine, arecoline, and the like;

31. Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine, and the like;

32. Mydriatics such as, atropine, cyclopentolate, homatropine, scopolamine, tropicamide, eucatropine, hydroxyamphetamine, and the like;

33. Psychic energizers such as 3-(2-aminopropy)indole, 3-(2-aminobutyl)indole, and the like;

34. Humoral agents such as, the prostaglandins, natural and synthetic, for example $PGE_1$, $PGE_{2\alpha}$, and $PGF_{2\alpha}$, and the $PGE_1$ analog misoprostol.

35. Antispasmodics such as, atropine, methantheline, papaverine, cinnamedrine, methscopolamine, and the like;

36. Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like;

37. Anti-diabetics such as, insulin, and anticancer drugs such as, tamoxifen, methotrexate, and the like;

38. Anorectic drugs such as, dextroamphetamine, methamphetamine, phenylpropanolamine, fenfluramine, diethylpropion, mazindol, phentermine, and the like;

39. Anti-allergenics such as, antazoline, methapyrilene, chlorpheniramine, pyrilamine, pheniramine, and the like;

40. Decongestants such as, phenylephrine, ephedrine, naphazoline, tetrahydrozoline, and the like;

41. Antipyretics such as, aspirin, salicylamide, and the like;

42. Antimigrane agents such as, dihydroergotamine, pizotyline, and the like;

43. Anti-malarials such as, the 4-aminoquinolines, alphaaminoquinolines, chloroquine, pyrimethamine, and the like;

44. Anti-ulcerative agents such as, misoprostol, omeprazole, enprostil, and the like;

45. Peptides such as, growth releasing factor, and the like;

46. Anti-estrogen or anti-hormone agents such as, tamoxifen or human chorionic gonadotropin, and the like;

47. Antiulcer agents such as, allantoin, aldioxa, alcloxa, N-methylscopolamine methylsuflate, and the like;

48. Antidiabetics, and the like.

The drugs mentioned above can be used in combination as required. Moreover, the above drugs may be used either in the free form or, if capable of forming salts, in the form of a salt with a suitable acid or base. If the drugs have a carboxyl group, their esters can be employed.

The acid mentioned above may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid or sulfuric acid. The base may be an organic base, for example, ammonia, triethylamine, or an inorganic base, for example, sodium hydroxide or potassium hydroxide. The esters mentioned above may be alkyl esters, aryl esters, aralkyl esters, and the like.

When a drug different than an anesthetic agent is used the solvent selected is one in which the drug is soluble. In generally the polyhydric alcohol can be used as a solvent for a wide variety of drugs. Other useful solvents are those known to solubilize the drugs in question.

What is claimed is:

1. A composition for topical application comprising:
   a. a therapeutically effective amount of at least one local anesthetic;
   b. a pharmaceutically acceptable solvent for the anesthetic, in an amount from about 5 to about 70 weight percent based on the weight of the whole composition;
   c. in admixture with the anesthetic agent in the solvent, a flexible, finite, pharmaceutically acceptable polysaccharide bioadhesive carrier in an amount from about 20 to about 50 weight percent based on the weight of the whole composition;
   wherein said composition contains less than 10% by weight water, is substantially water insoluble and is a bioadhesive.

2. The composition of claim 1, wherein the anesthetic agent is selected from the group consisting of procaine, lidocaine, prilocaine, mepivacaine, dyclonine, dibucaine, benzocaine, chloroprocaine, tetracaine, bupivacaine, and etidocaine.

3. The composition of claim 2, wherein the anesthetic agent is in the form of the base or an acid-addition salt or both forms.

4. The composition of claim 3, wherein the acid-addition salt is hydrochloride.

5. The composition of claim 1, wherein the bioadhesive is selected from the group consisting of gums and celluloses.

6. The composition of claim 5, wherein the gum is selected from the group consisting of karaya gum, tragacanth gum, pectin gum, xanthan gum, guar gum, cellulose, and cellulose derivatives.

7. The composition of claim 1, wherein the solvent for the anesthetic agent is at least one polyhydric alcohol.

8. The composition of claim 7, wherein the polyhydric alcohol is a polyalkylene glycol.

9. The composition of claim 8, wherein the glycol is selected from the group consisting of dipropylene glycol, propylene glycol, ethylene glycol, polyethylene glycol, glycerin, butylene glycol, hexylene glycol, polypropylene glycol, and sorbitol.

10. The composition of claim 1, further comprising a backing material conforming to the size and shape of a single dosage of the composition.

11. A composition for topical application comprising:
    a. a therapeutically effective amount of a first local anesthetic agent in base form;
    b. a therapeutically effective amount of a different, second local anesthetic agent in acid-addition salt form;
    c. a solvent for the first and second local anesthetic agents in an amount from about 5 to about 70 weight percent based on the weight of the whole composition; and
    d. in an admixture with the anesthetic agents in the solvent, a flexible, finite, pharmaceutically acceptable, bioadhesive carrier in an amount from about 20 to about 50 weight percent based on the weight of the whole composition;
    wherein the composition is substantially free of water and is substantially water insoluble.

12. The composition of claim 11, wherein the first local anesthetic agent in base form is selected from the group consisting of procaine, lidocaine, prilocaine, mepivacaine, dyclonine, dibucaine, benzocaine, propoxycaine, and chloroprocaine.

13. The composition of claim 11, wherein the second local anesthetic agent in acid-addition salt form is selected from the group consisting of a dyclonine salt, a prilocaine salt, a tetracaine salt, a bupivacaine salt, a mepivacaine salt, a lidocaine salt, a procaine salt, an etidocaine salt and a dibucaine salt.

14. The composition of claim 11, wherein the first local anesthetic agent in base form is selected from the group consisting of procaine, dyclonine, lidocaine, prilocaine, mepivacaine, benzocaine, propoxycaine and chloroprocaine and the second local anesthetic agent in acid-addition salt form is selected from the group consisting of a dyclonine salt, a prilocaine salt, a tetracaine salt, a bupivacaine salt, a mepivacaine salt, a lidocaine salt, a procaine salt, an etidocaine salt, and a dibucaine salt.

15. The composition of claim 14, wherein the acid-addition salt is the hydrochloride.

16. The composition of claim 15, wherein the bioadhesive is selected from the group consisting of polyacrylates, polyacrylic acids, gums and celluloses.

17. The composition of claim 16, wherein the gum is selected from the group consisting of karaya gum, tragacanth gum, pectin gum, xanthan gum and guar gum.

18. The composition of claim 11, wherein the solvent for the anesthetic agents is at least one polyhydric alcohol.

19. The composition of claim 18, wherein the polyhydric alcohol is a polyalkylene glycol.

20. The composition of claim 19, wherein the glycol is selected from the group consisting of dipropylene glycol, propylene glycol, ethylene glycol, polyethylene glycol, glycerin, butylene glycol, hexylene glycol, polypropylene glycol, and sorbitol.

21. The composition of claim 11 further comprising a backing material which conforms to the size and shape of a single dosage of the composition.

22. The composition of claim 1, wherein said composition contains less than 5% by weight water.

23. The composition of claim 1, wherein said composition contains less than 3% by weight water.

* * * * *